United States Patent [19]

Merbach

[11] Patent Number: 5,461,744
[45] Date of Patent: Oct. 31, 1995

[54] DENTAL DEVICE ATTACHABLE TO AN ELECTRIC TOOTHBRUSH DRIVE

[75] Inventor: Lothar Merbach, Frankfurt, Germany

[73] Assignee: Rowenta-Werke GmbH, Offenbach am Main, Germany

[21] Appl. No.: 338,621

[22] PCT Filed: Mar. 12, 1994

[86] PCT No.: PCT/DE94/00264

§ 371 Date: Nov. 18, 1994

§ 102(e) Date: Nov. 18, 1994

[87] PCT Pub. No.: WO94/21193

PCT Pub. Date: Sep. 29, 1994

[30] Foreign Application Priority Data

Mar. 20, 1993 [DE] Germany ............... 9304184 U

[51] Int. Cl.⁶ ............. A61C 17/32; A46B 13/02
[52] U.S. Cl. ....................... 15/22.1; 74/99 R
[58] Field of Search ................. 15/22.1, 22.2, 15/22.4, 28, 29; 74/89, 99 R; 433/131, 216, 125

[56] References Cited

U.S. PATENT DOCUMENTS

| | | | |
|---|---|---|---|
| 4,989,287 | 2/1991 | Scherer | 15/22.1 |
| 5,177,826 | 1/1993 | Vrignaud | 15/22.1 |
| 5,213,434 | 5/1993 | Hahn | 15/22.1 |

FOREIGN PATENT DOCUMENTS

| | | | |
|---|---|---|---|
| 0500517 | 2/1939 | United Kingdom | 15/22.1 |

*Primary Examiner*—Edward L. Roberts, Jr.
*Attorney, Agent, or Firm*—Cohen, Pontani, Lieberman, Pavane

[57] ABSTRACT

A dental device for an electric toothbrush drive having a drive shaft, the dental device including a housing, a motion converter arranged in the housing and including a rocker arm, a rotary oscillation plate having an eccentrically arranged plug-in opening, and a plug-in axle for operatively connecting the rotary oscillation plate to the rocker arm via the plug-in opening. A guide is provided for releasably and operatively connecting one end of the rocker arm to the drive shaft of the toothbrush drive, and a bearing is provided for rotatably supporting the rotary oscillating plate at the housing. The motion converter converts the movement of the drive shaft into rotational ocillatory movement of the rotary oscillation plate about the plug-in axle.

4 Claims, 1 Drawing Sheet

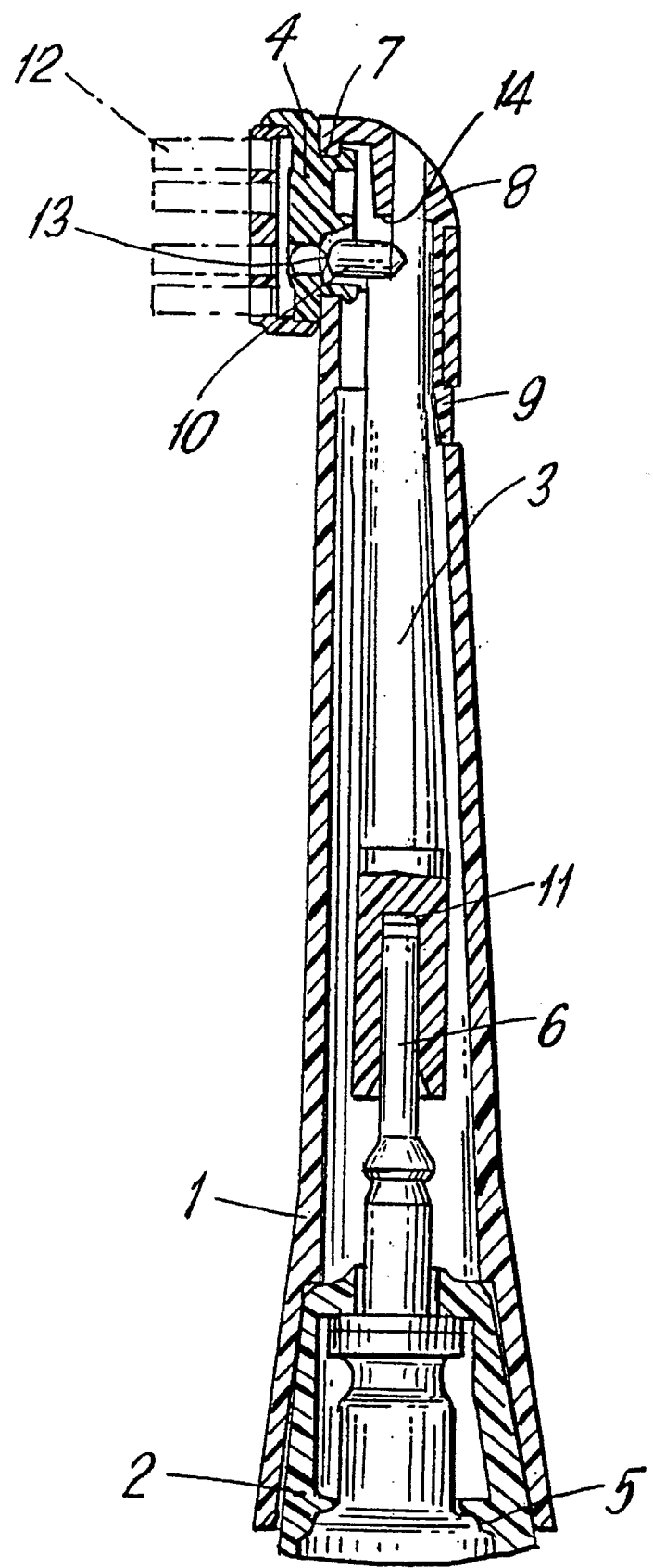

DENTAL DEVICE ATTACHABLE TO AN ELECTRIC TOOTHBRUSH DRIVE

BACKGROUND OF THE INVENTION

1. Field of the Invention

The invention is directed to an attachable dental device for an electric toothbrush drive with a housing and a motion converter arranged in the housing.

2. Description of the Prior Art

An electric toothbrush with a drive mechanism is known from EP-OS 0 357 863. The drive mechanism has an electric motor, a motion converter which is arranged between the motor and the attachable shaft, and a brush body constructed as an attachment. The motion converter sets the attachable shaft in radial and longitudinal motion. The motor and motion converter are arranged in a housing. In the installed state, the attachment is connected with the housing of the toothbrush drive mechanism so as to be rotatable. A rocker arm is supported in the attachment in such a way that the rocker arm can only carry out longitudinal movements, but not radial movements. The rocker arm is detachably connected with the attachable axle of the electric drive mechanism via a catch connection. A plurality of brushes which are set in radial motion by the rocker arm by means of an eccentric drive are supported in the attachment. During operation, the movement of the attachable shaft is transmitted in such a way that the entire attachment executes radial movements, while the longitudinal movements of the rocker arm, after being converted at the eccentric drive, allow the brushes to additionally carry out radial movements. Since not only the brushes, but the entire attachment, i.e., the housing and brushes, carry out additional radial movements, it is not possible to clean the spaces between teeth or to polish the teeth even when only one brush is attached because of these radial movements. Moreover, the energy consumed by the drive mechanism is very high and is further increased when the catch connection between the drive mechanism and attachment is soiled by toothpaste.

SUMMARY OF THE INVENTION

The object of the present invention is to expand the range of application of an electric toothbrush drive while avoiding the disadvantages mentioned above by providing a treatment device which can polish teeth and clean the spaces between teeth, which device is attachable to the electric toothbrush drive. The dental treatment tool which is designed as a polishing and/or cleaning device carries out exclusively rotational oscillations.

Pursuant to this object, and others which will become apparent hereafter, one aspect of the present invention resides in a device attachable to an electric toothbrush drive, which device includes a motion converter arranged in a housing. The motion converter converts the movement of the driveshaft of the toothbrush drive into rotational oscillatory movement of a rotary oscillation plate.

The range of application of an electric toothbrush drive is expanded by the attachable device according to the invention. In addition to conventional attachable toothbrushes which already carry out radial and longitudinal movements, devices, e.g., for polishing teeth or for cleaning the spaces between teeth, which carry out exclusively rotational oscillations can be driven by the same drive mechanism. The rocker arm is supported in the interior of the attachable device according to the invention and during operation one end of the rocker arm is in a working connection with the drive shaft of the drive mechanism. The other end of the rocker arm remote of the drive shaft is in a working connection with the radial drive for a dental treatment tool. The drive shaft carries out rotational movements having axial and radial components. The motion converter, which has a rocker arm, the rotary oscillation plate, an attachable or plug-in axle and an insertion or plug-in opening, converts these rotational movements into a movement of the rotary oscillation plate, which movement carries out rotational oscillations. A polishing and/or cleaning device which executes exclusively rotational oscillations is connected with the rotary oscillation plate. The end of the attachable device remote of the drive shaft of the drive mechanism is constructed as a two-part bearing for the radial drive. One bearing part is a structural component of the housing and the other bearing part is constructed as a cap which is detachably fastened to the housing by means of a snap connection. The attachable device according to the invention is advantageously formed by four individual parts which can be produced inexpensively as plastic injection molded parts and can be assembled in a simple manner without additional tools.

BRIEF DESCRIPTION OF THE DRAWINGS

An embodiment of the device pursuant to the present invention is shown in section in the drawing.

DETAILED DESCRIPTION OF THE PREFERRED EMBODIMENTS

The attachable dental treatment device shown in the drawing has a housing 1 in which a motion converter 3, 4 is supported so as to be freely movable. The motion converter 3, 4 essentially has a rocker arm 3 and a rotary oscillation plate 4. The, inventive device is detachably held at a toothbrush drive 2 by means of a catch connection 5. The rocker arm 3 is in a working connection with the drive shaft 6 of the toothbrush drive 2. The end of the housing 1 remote of the catch connection 5 is constructed as a two-part rotating bearing 7 for the rotary oscillation plate 4. One half of the rotating bearing 7 is in the form of a cap 8 which is connected with the housing 1 by means of a snap connection 9. A plug-in axle 10 is arranged at the rocker arm 3, preferably at a right angle to the axis of the rocker arm 3. The rocker arm 3 is in a working connection with the rotary oscillation plate 4 via the plug-in axle 10. A limiting stop 14 for the plug-in axle 10 is provided at the cap 8. The end of the rocker arm 3 remote of the plug-in axle 10 is constructed as a guide 11 for the drive shaft 6 of the toothbrush drive 2. During operation, the rotating movement of the drive shaft 6 having axial and radial components is transformed into a movement of the rotary oscillation plate ,4, which movement carries out rotational oscillations around the plug-in axle 10. In an advantageous manner, the resulting angle of rotation by which the rotary oscillation plate 4 oscillates is greater than the radial oscillating angle of the drive shaft 6. The transformation is effected via the rocker arm 3 which is connected with the drive shaft 6 and via the plug-in axle 10 which is arranged at the rocker arm 3 and is in a working connection with the rotary oscillation plate 4 via an eccentrically arranged plug-in opening 13. The transmission ratio of the motion converter can be adjusted by suitably dimensioning the length of the plug-in axle 10 and appropriate eccentricity of the plug-in opening 13. The dental treatment tool 12 held at the rotary oscillation plate 4 accordingly carries out a rotating movement which oscillates around a rotational angle.

I claim:

1. A dental device for an electric toothbrush drive having a drive shaft which undergoes movement having axial and radial components, comprising: a housing; motion converter means arranged in the housing and including a rocker arm, a rotary oscillation plate having an eccentrically arranged plug-in opening, and a plug-in axle for operatively connecting the rotary oscillation plate to the rocker arm via the plug-in opening; guide means for releasably and operatively connecting one end of the rocker arm to the drive shaft of the toothbrush drive; and bearing means for rotatably supporting the rotary oscillating plate at the housing, the motion converter means converting the movement of the drive shaft into rotational oscillatory movement of the rotary oscillation plate about the plug-in axle.

2. A dental device as claimed in claim 1, wherein the plug-in axle is arranged at a right angle to the rocker arm.

3. A dental device as claimed in claim 1, wherein the bearing means is arranged at an end of the housing remote of the toothbrush drive shaft and is constructed as a two-part rotating bearing having a first part formed as a cap, and further comprising means for detachably connecting the cap to the housing.

4. A dental device as defined in claim 1, and further comprising a dental treatment tool detachably connected with the rotary oscillation plate.

* * * * *